US005783389A

United States Patent [19]
Vo-Dinh

[11] Patent Number: 5,783,389
[45] Date of Patent: Jul. 21, 1998

[54] SURFACE ENHANCED RAMAN GENE PROBE AND METHODS THEREOF

[75] Inventor: Tuan Vo-Dinh, Knoxville, Tenn.

[73] Assignee: Lockheed Martin Energy Research Corporation, Oak Ridge, Tenn.

[21] Appl. No.: 791,981

[22] Filed: Jan. 31, 1997

Related U.S. Application Data

[62] Division of Ser. No. 543,212, Oct. 13, 1995.

[51] Int. Cl.$^6$ .............................. C12Q 1/68; C12P 19/34
[52] U.S. Cl. ............................................ 435/6; 435/91.2
[58] Field of Search .................................... 435/6, 91.2

[56] References Cited

U.S. PATENT DOCUMENTS

| | | | |
|---|---|---|---|
| 4,674,878 | 6/1987 | Vo-Dinh | 356/301 |
| 5,306,403 | 4/1994 | Vo-Dinh | 204/182.8 |
| 5,325,342 | 6/1994 | Vo-Dinh | 369/13 |
| 5,400,136 | 3/1995 | Vo-Dinh | 356/301 |

OTHER PUBLICATIONS

Schofield, Nucleic Acid Res 17(22):9498, 1989.
D. J. Jeanmaire, R. P. Van Duyne, *J. Electronal. Chem.*, 84, 1977.
G. Whitesides, P. Laibnis, *Langmuir*, 6, pp. 87–95, 1990.
A. Pal et al, *Analytical Chemistry*, 67, p. 3154, 1995.
Yung–Fong Cheng et al, *Applied spectroscopy*, 44, pp. 755–765, 1990.
Tuan Vo–Dinh et al, *Anal. Chemistry*, 66, pp. 3379–3383, 1994.

*Primary Examiner*—Eggerton A. Campbell
*Attorney, Agent, or Firm*—Shelley L. Stafford

[57] ABSTRACT

The subject invention disclosed herein is a new gene probe biosensor and methods thereof based on surface enhanced Raman scattering (SERS) label detection. The SER gene probe biosensor comprises a support means, a SER gene probe having at least one oligonucleotide strand labeled with at least one SERS label, and a SERS active substrate disposed on the support means and having at least one of the SER gene probes adsorbed thereon. Biotargets such as bacterial and viral DNA, RNA and PNA are detected using a SER gene probe via hybridization to oligonucleotide strands complementary to the SER gene probe. The support means supporting the SERS active substrate includes a fiberoptic probe, an array of fiberoptic probes for performance of multiple assays and a waveguide microsensor array with charge-coupled devices or photodiode arrays.

3 Claims, 12 Drawing Sheets

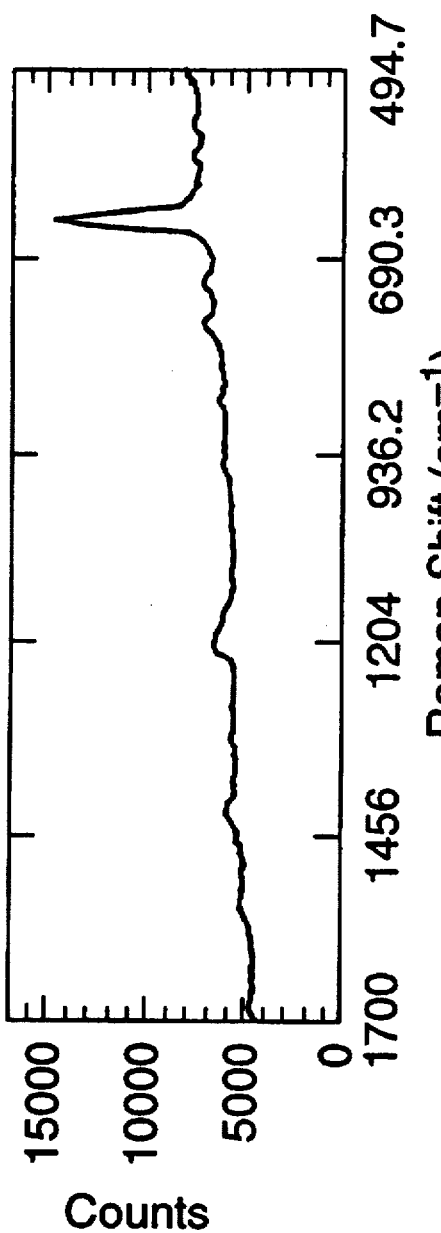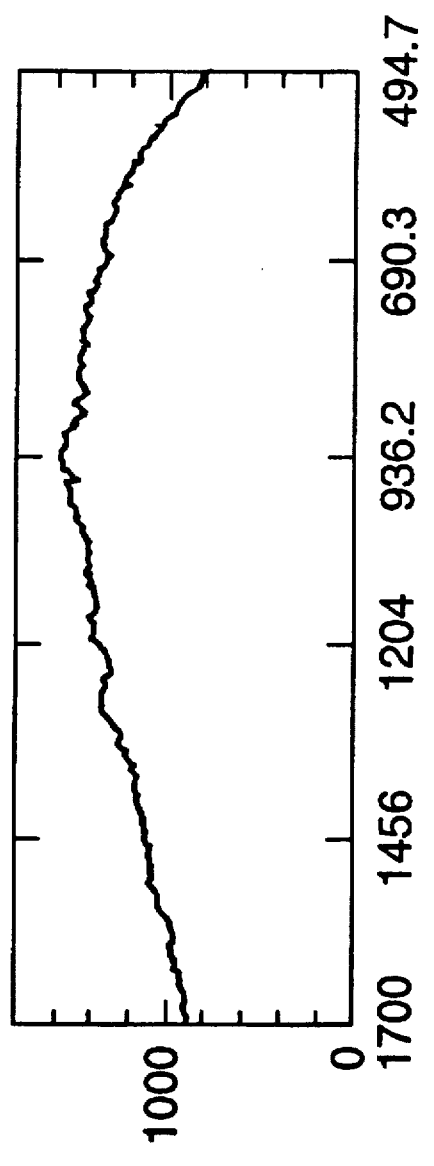
Fig. 4a
Fig. 4b

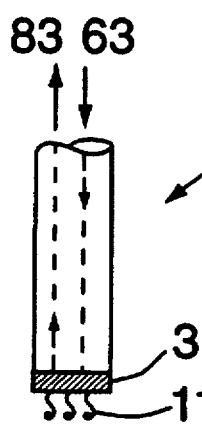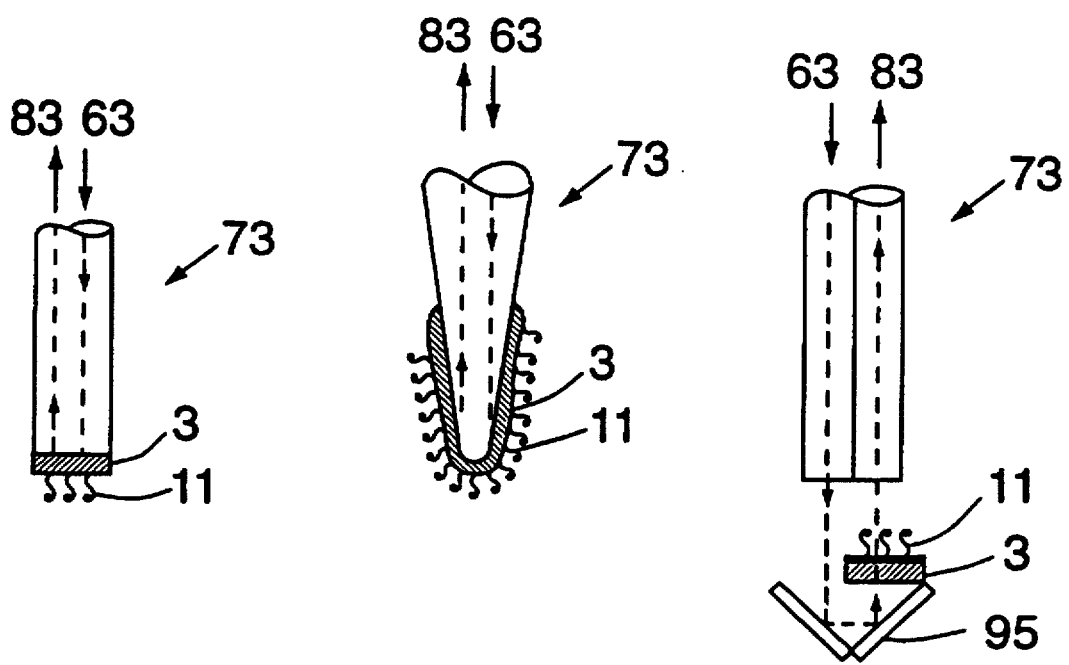
Fig. 8a  Fig. 8b  Fig. 9

SURFACE ENHANCED RAMAN GENE PROBE AND METHODS THEREOF

CROSS REFERENCE TO RELATED APPLICATION

This application is a divisional of application Ser. No. 08/543,212 filed on Oct. 13,1995.

This invention was made with Government support under contract DE-AC05-84OR21400 awarded by the Office of Health and Environmental Research, Department of Energy to Lockheed Martin Energy Systems, Inc., and the Government has certain rights in this invention.

FIELD OF THE INVENTION

The present invention relates to DNA gene probes, biosensors and methods for gene identification, particularly non-radioactive gene probes, biosensors and methods for oligonucleotide identification and more particularly to non-radioactive gene probes, biosensors and methods based on surface enhanced Raman scattering (SERS) label detection.

BACKGROUND OF THE INVENTION

There is currently strong interest in the development of nonradioactive DNA probes for use in a wide variety of applications, such as gene identification, gene mapping, DNA sequencing, medical diagnostics, and biotechnology. Among the various methods for gene identification, technologies using radioactive labels are currently the most widely used. Radioactive label techniques suffer from several disadvantages however. The principal isotope used, Phosphorus-32, has a limited shelflife because it has a 14-day half-life. Secondly, because there is one principal label for gene probes, DNA can only be probed for one sequence at a time. Due to material limitations, probing immobilized DNA with different $^{32}$P-labeled sequences can only be performed a few (3–4) times. Therefore, the researcher must have idea about the sequence prior to probing. In addition to these inconveniences, the potential safety hazard associated with use of radioactive materials makes the technology undesirable. Shipping, handling and waste disposal of radioactive materials are strictly regulated by federal and state guidelines.

Recently, luminescence labels such as fluorescent or chemiluminescent labels have been developed for gene detection. Although sensitivities achieved by luminescence techniques are adequate, alternative techniques with improved spectral selectivities must be developed to overcome the need for radioactive labels and the poor spectral specificity of luminescent labels.

Spectroscopy is an analytical technique concerned with the measurement of the interaction of radiant energy with matter and with the interpretation of the interaction both at the fundamental level and for practical analysis. Interpretation of the spectra produced by various spectroscopic instrumentation has been used to provide fundamental information on atomic and molecular energy levels, the distribution of species within those levels, the nature of processes involving change from one level to another, molecular geometries, chemical bonding, and interaction of molecules in solution. Comparisons of spectra have provided a basis for the determination of qualitative chemical composition and chemical structure, and for quantitative chemical analysis.

Vibrational spectroscopy is a useful technique for characterizing molecules and for determining their chemical structure. The vibrational spectrum of a molecule, based on the molecular structure of that molecule, is a series of sharp lines which constitutes a unique fingerprint of that specific molecular structure. If the vibrational spectrum is to be measured by an optical absorption process, optical fibers must be used so that optical energy from a source is delivered to a sample via one fiber, and after passage through the sample, an optical signal generated by the exciting optical energy is collected by the same or, more preferably, another fiber. This collected light is directed to a monochrometerlor a photodetector for analyzing its wavelength and/or intensity.

One particular spectroscopic technique, known as Raman spectroscopy, utilizes the Raman effect, which is a phenomenon observed in the scattering of light as it passes through a material medium, whereby the light suffers a change in frequency and a random alteration in phase. When exciting optical energy of a single wavelength interacts with a molecule, the optical energy scattered by the molecule contains small amounts of optical energy having wavelengths different from that of the incident exciting optical energy. The wavelengths present in the scattered optical energy are characteristic of the structure of the molecule, and the intensity of this optical energy is dependent on the concentration of these molecules.

Raman spectroscopy is a spectrochemical technique that is complementary to fluorescence, and has been an important analytical tool due to its excellent specificity for chemical group identification. Raman spectroscopy provides a means for obtaining similar molecular vibrational spectra over optical fibers using visible or near infrared light that is transmitted by the optical fibers without significant absorption losses. In Raman spectroscopy, monochromatic light is directed to a sample and the spectrum of the light scattered from the sample is determined. One of the major limitations of Raman spectroscopy is its low sensitivity. Recently, the Raman technique has been rejuvenated following the discovery of enormous Raman enhancement of up to $10^6$ for molecules adsorbed on microstructures of metal surfaces.

Raman spectroscopy is a useful tool for chemical analysis due to its excellent capability of chemical group identification. One limitation of conventional Raman spectroscopy is its low sensitivity, often requiring the use of powerful and costly laser sources for excitation. However, a renewed interest has recently developed among Raman spectroscopists as a result of observation that Raman scattering efficiency can be enhanced by factors of up to $10^8$ when a compound is adsorbed on or near special metal surfaces. Spectacular enhancement factors due to the microstructured metal surface scattering process is responsible for increasing the intrinsically weak normal Raman scattering (NRS). The technique associated with this phenomenon is known as surface-enhanced Raman scattering (SERS) spectroscopy. The Raman enhancement process is believed to result from a combination of several electromagnetic and chemical effects between the molecule and the metal surface.

Deoxyribonucleic acid (DNA) is the main carrier of genetic information in most living organisms. DNA is essentially a complex molecule built up of deoxyribonucleotide repeating units. Each unit comprises a sugar, phosphate, and a purine or pyrimidine base. The deoxyribonucleotide units are linked together by the phosphate groups, joining the 3' position of one sugar to the 5' position of the next. The alternate sugar and phosphate residues form the backbone of the molecule, and the purine and pyrimidine bases are attached to the backbone via the 1' position of the deoxyribose. This sugar-phosphate backbone is the same in all DNA molecules. What gives each DNA its individuality is the sequence of the purine and pyrimidine bases.

OBJECTS OF THE INVENTION

It is an object of the invention to provide a nonradioactive gene probe biosensor based upon surface enhanced Raman scattering (SERS) label detection for identifying target oligonucleotide strands such as Deoxyribonucleic acid (DNA), Ribonucleic acid (RNA) and Peptide nucleic acid (PNA) in a variety of samples such as environmental samples or biological samples. It is another object of the invention to provide a SERS gene probe biosensor for the identification of bacterial and viral gene sequences.

It is a further object of the invention to provide a SERS gene probe detection system for the detection and identification of biotargets such as DNA, RNA and PNA in bacteria and viruses. It is yet another object of the invention to provide methods for using a SERS gene probe biosensor for hybridization, detection and identification of hybridized target oligonucleotides such as DNA, RNA and PNA in bacteria and viruses in a variety of samples such as environmental or biological samples. Further and other objects of the present invention will become apparent from the description contained herein.

SUMMARY

The subject invention is a new type of gene probe biosensor based on surface enhanced Raman scattering label detection. The surface enhanced Raman (SER) gene probes do not require the use of radioactive labels and have great potential to provide both sensitivity and selectivity. The SER gene probe is used to detect DNA biotargets such as gene sequences, bacteria and viral oligonucleotide strands via hybridization to oligonucleotide strands complementary to the SER gene probe.

In accordance with one object of the invention, a SER gene probe biosensor comprises a support means, a SER gene probe having at least one oligonucleotide strand labeled with at least one SERS label, and a SERS active substrate disposed on the support means and having at least one of the SERS gene probe adsorbed thereon.

In accordance with another object of the invention, a SER gene probe detection system comprises a SERS active substrate having at least one SER gene probe adsorbed thereon wherein the SER gene probe has at least one oligonucleotide strand labeled with at least one SERS label. The system further comprises an energy source, a means for transmitting optical energy from an optical energy source to the SERS active substrate in order to generate a Raman signal, a means for collecting the Raman signal and transmitting the Raman signal for detection, and an analyzing means for detecting and processing the Raman signal.

In accordance with yet another object of the invention, a method for using a SER gene probe for hybridization and detection to identify hybridized target oligonucleotide strands comprising the steps of: a) preparing a sampling medium with immobilized oligonucleotide strands of known sequence adsorbed thereon wherein the immobilized oligonucleotide strands are complementary to the target oligonucleotide strands; b) synthesizing SER gene probes wherein a SER gene probe comprises at least one oligonucleotide strand of unknown sequence having at least one SERS active label; c) preparing a SER gene probe solution comprising at least one SER gene probe wherein the SERS label is unique to the oligonucleotide strand of a particular sequence; d) incubating the sample medium in an amount of SER gene probe solution sufficient enough to hybridize the immobilized oligonucleotide strands on the sample medium with the target oligonucleotide strands that are complementary to the immobilized oligonucleotde strands, incubating for a time period sufficient enough as for the SER gene probes to contact the immobilized oligonucleotide strands and sufficient enough as for hybridization to occur, thereby producing hybridized oligonucleotde material; e) removing the oligonucleotide strands that did not hybridize to the immobilized oligonucleotide strands; f) recovering the hybridized oligonucleotide material from the sampling medium; g) transferring to a SERS active substrate a small amount of the recovered hybridized oligonucleotide material in an amount sufficient enough as to provide a detectable quantity of hybridized oligonucleotide material; and h) analyzing the SERS active substrate containing the hybridized oligonucleotide material.

In accordance with still another object of the invention, a method for using a SER gene probe for hybridization and direct detection to identify hybridized target oligonucleotide strands comprising the steps of: a) preparing a SERS active substrate having adsorbed thereon at least one SER gene probe complementary to the target oligonucleotide strand wherein the SER gene probe comprises at least one oligonucleotide strand of known sequence labeled with a SERS label unique for the target oligonucleotide strands of a particular sequence; b) introducing the SERS active substrate into a sample suspected of containing target oligonucleotide strands and contacting the SER gene probe with the target oligonucleotide strands for a time sufficient enough as for the contact to occur and hybridization to occur between the target oligonucleotide strand and the complementary SER gene probe, thereby producing hybridized oligonucleotide material; c) removing from the SERS active substrate, remaining sample containing nonhybridized oligonucleotide strands; and d) analyzing the SERS active substrate containing the hybridized oligonucleotide material.

In accordance with still yet another object of the invention, a method for using a SER gene probe for detection and identification of target DNA strands that have been amplified through Polymerase Chain Reaction comprising the steps of: a) preparing a SERS active substrate having adsorbed thereon two unlabeled DNA strands of known sequence, being complementary to a target region of a target DNA strand, said target DNA strand comprising double strands of DNA complementary to one another, and said SERS active substrate being disposed on a support means; b) synthesizing two SER gene probes as primers wherein each of said SER gene probes comprises an oligonucleotide strand complementary to sites on the opposite DNA strands of said target DNA strand wherein each primer has a sequence which is identical to the 5' end of one DNA strand of said target DNA strand, each of said SER gene probes further comprises a SERS label attached to said oligonucleotide strand; c) heating said target DNA strand to a temperature sufficient for denaturization of said double strands of said target DNA to occur to form single-stranded DNA templates; d) annealing said two primers to said DNA templates at a temperature ranging from 40°–60° C. wherein each primer binds to said complementary sequence at the 3' end of said opposite DNA strand of said target DNA strand; e) adding DNA polymerase to extend the DNA molecule through said target region of said target DNA strand yielding amplified products, said amplified products being SERS labeled amplified DNA segments; f) immersing said SERS active substrate in a sample containing said amplified products; g) incubating said SERS active substrate in said sample for a time sufficient enough as for hybridization between said SERS labeled amplified DNA segments and said unlabeled DNA strands on said substrate to occur to completion and a SERS signal is detected; and h) analyzing said SERS signal.

BRIEF DESCRIPTION OF THE DRAWINGS

For a better understanding of the present invention, together with other and further objects, advantages and capabilities thereof, reference is made to the following disclosure and appended claims when read in connection with the appended drawings, wherein:

FIG. 4a is a spectrum showing detection of the SER Gene Probe that has hybridized to a DNA fragment complementary to the probe.

FIG. 4b is a spectrum showing no SERS detection.

FIG. 8 shows a close-up view of the dotted area of the SER Gene Probe Fiberoptic Biosensor in FIG. 7 with SER Gene Probes being attached to the SERS active substrate on the fiberoptic probe tip.

FIG. 9 shows an alternate embodiment to the SER Gene Probe Fiberoptic Biosensor of FIG. 8.

DETAILED DESCRIPTION OF THE INVENTION

Figure 1:
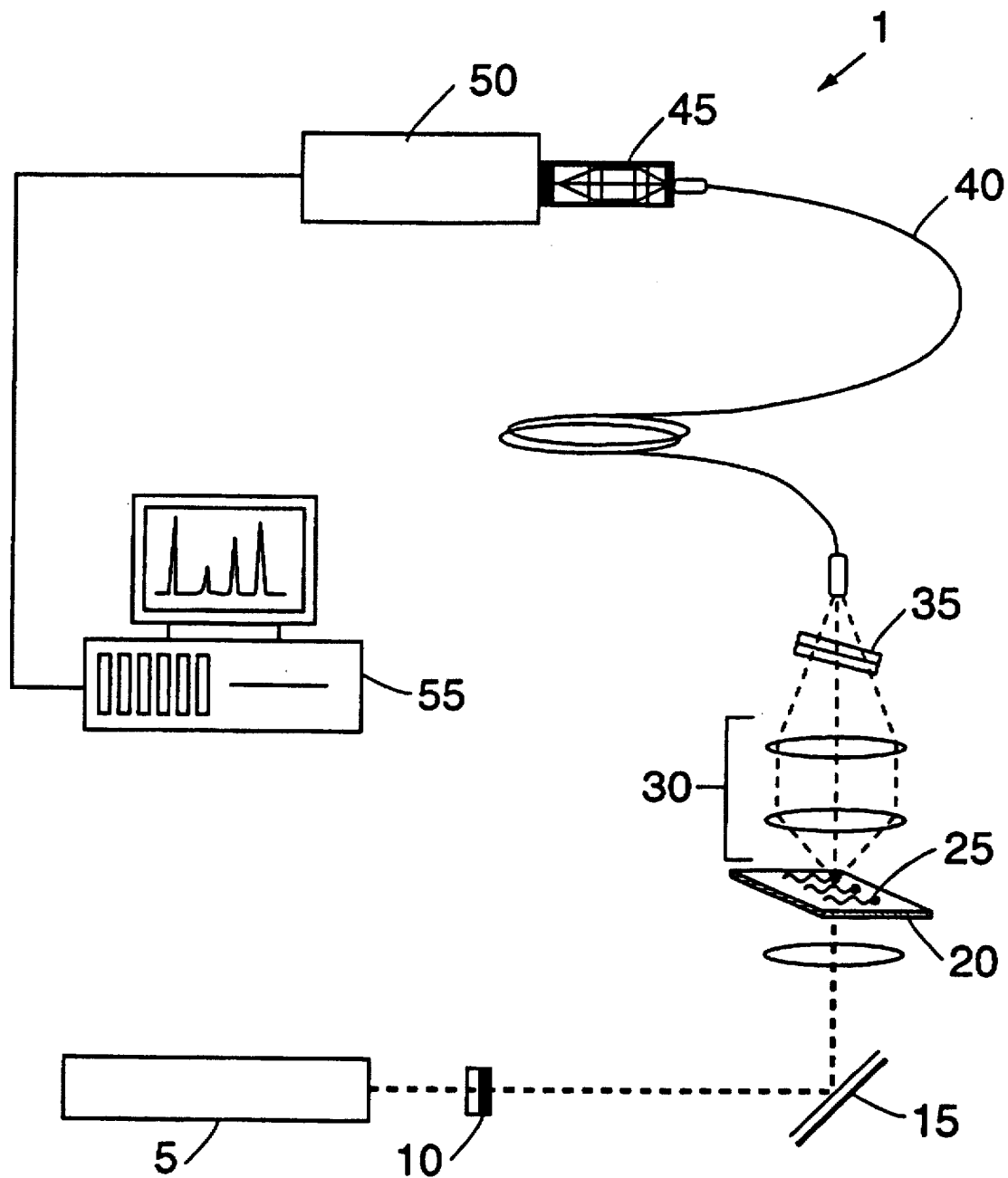
FIG. 1 illustrates a SER Gene Probe Detection System.

The possibility of using Raman and/or SERS for in situ monitoring has been reported in the past few years as well as development of efficient SERS active substrates for trace organic analysis in environmental and biological applications. The SERS technique has also been applied to trace detection of pesticides, dyes, food products, and metabolites of chemical exposure. The subject invention herein discloses the use of the SERS technique as a tool for detecting specific nucleic acid sequences. An example of a hybridization experiment using the SER gene probe illustrates the usefulness of this technology. Hybridization of a nucleic acid probe to DNA biotargets such as gene sequences, bacteria and viral DNA permits a very high degree of accuracy for identifying DNA sequences complementary to that probe.

Applicant's SERS gene probe technology can rapidly detect microorganisms from multiple environmental samples. Examples include detection of Salmonella bacteria, the causative agent for food poisoning, during food processing; detection of Legionaella bacteria, the causative agent for pneumonia, from water samples; detection of Giardlia lamblia, causative agent for diarrhea, from water samples; and detection of Hepatitis virus from shellfish. Applicant's SERS gene probe biosensor can also have a global impact on biosensor technology in cancer detection. Applicant's biosensor is able to detect both DNA and RNA viruses and retroviruses in particular which can play a part in transforming healthy cells into cancer cells. Examples of this global impact include the detection of DNA viruses such as Papovavirus and its many strains which play a part in causing benign warts and carcinoma of uterine cervix worldwide. The detection of Hepadnavirus (Hepatitis B), which plays a part in causing liver cancer mainly in southeast Asia and tropical Africa, is now possible. Also, the detection of Herpesvirus, which plays a role in causing lymphocyte cancer and nasopharyngeal carcinoma mainly in west Africa, southern China and Greenland. Applicant's probe can also make a global impact on the detection of the HIV-1 virus, the causative agent for Kaposi's carcinoma and AIDS, worldwide. Another example is the detection of human T-cells and HTLV-1 virus which play a part in adult T-cell mainly in Japan (Kyushu) and detection of leukemiallymphoma, mainly in the West Indes. Applicant's probe is a sensitive DNA biosensor that can detect viral diseases at the early stage of the infection. Yet other viruses and bacteria that can be detected are included in the causative agents that play a role in AIDS, Lyme Disease, Rocky Mountain Spotted Fever, Tuberculosis, Toxoplasmosis and Cancer. These bacteria and viruses can dwell in numerous different mediums which can be analyzed by Applicant's SERS gene probe biosensor. These different mediums include bodily fluids, blood, sputum, cat feces, raw meat and other tissues.

Applicant's invention is a Surface Enhanced Raman (SER) gene probe biosensor used for the detection and identification of hybridized oligonucleotide strands labeled with a SERS label wherein identification of a target oligonucleotide is based on the detection of the SERS label. The SER gene probe biosensor comprises a support means, a SER gene probe and a SERS active substrate disposed on the support means. The SERS active substrate has at least one SERS gene probe adsorbed onto the substrate. The SER gene probe has at least one oligonucleotide strand labeled with at least one SERS label. Oligonucleotides include DNA, RNA and PNA. The oligonucleotide of the SER gene probe either has the SERS label attached to the strand or if two oligonucleotide strands are used, the SERS label can be intercalated between the two oligonucleotide strands, enveloped by the oligonucleotide strands holding the label in place. If the SERS label is attached to the oligonucleotide strand, the label can be attached either at the end of the strand or at any site between the strand ends. More than one SERS label can be used to label as long as it does not interfere with hybridization. Many different SERS labels can be used. Examples of the different SERS labels that can be used include cresyl fast violet, cresyl blue violet, para-aminobenzoic acid, erythrosin and aminoacridine. Other SERS labels that can be used that are inert to hybridization are chemical elements or structures that exhibit a characteristic Raman or SERS emission. These chemical elements or structures include cyanide, a methyl group, a thiol group, a chlorine, bromine, phosphorus and sulfur.

In one embodiment, Applicant's invention requires the oligonucleotide strand to be labeled with a SERS label for detection and identification. In another embodiment, a SERS label can be entrapped or intercalated into a double strand of oligonucleotide. The label is a specific chemical group that can be detected using the SERS spectrographic technique. Raman spectroscopy is a spectrochemical technique that is complementary to fluorescence, and is an important analytical tool due to its excellent specificity for chemical group identification. Recently, however, there has been enormous Raman enhancement of up to $10^8$ for molecules adsorbed on SERS active substrates, microstructures of metal surfaces. See, for example, D. J. Jeanmaire and R. P. Van Duyne *J. Electronal. Chem.*, 84, (1977).

The SERS active substrate includes a support base having a roughened metal surface having a degree of roughness sufficient to induce the SERS effect described above. The roughened surface is preferably formed by applying a microparticle or microstructure layer to the surface of the support base and then depositing a metal layer onto the microstructure layer. The roughened surface may be formed using conventional techniques, such as described in U.S. Pat. No. 4,674,878, incorporated herein by reference.

For the SERS active substrate to be effective for detecting and identifying a target oligonucleotide strand, the target oligonucleotide strand must be in the vicinity of the roughened surface. An overcoat of silica, metal oxides, self-assembled organic monolayer layer or organic polymer can be applied to the metallic microstructure layer. The coating is applied to the roughened surface to sorb the oligonucleotide material which are not easily adsorbed by the roughened surface and which are capable of either penetrating into the coating or being attached onto the coating. The oligonucleotide material thereby is adsorbed and becomes positioned in the vicinity of the roughened surface and exhibit the SERS effect. Thus, in essence, the coating serves to "alter" the adsorptivity of the roughened surace. The oligonucleotide material immobilized on the roughened surface of the SERS active substrate comprises either the labeled SER gene probe immobilized on the SERS active substrate which later hybridizes with the target oligonucleotide strand before analysis or it comprises an oligonucleotide strand of known sequence immobilized on the SERS active substrate which later hybridizes to the SERS labeled target oligonucleotide strand of unknown sequence. Therefore, the SER gene probe can be immobilized on the SERS active substrate before hybridization with a target oligonucleotide strand FIG. 6 or the SER gene probe is attached to an known oligonucleotide sequence complementary to a target oligonucleotide strand and is hybridized to the immobilized oligonucleotide strand on the substrate.

The coating may be an organic or inorganic sorbent material such as silica or self-assembled organic monolayer, or is an organic sorbent polymer coating, such as polymethyl-methacrylate. Selection of the polymer is based on the sorbtivity of the polymer for the oligonucleotide material to be identified. Selection criteria for coatings may be based upon the desired physical (e.g., size selectivity, permeability), chemical (e.g. polarity, chemical selectivity), electrical, magnetic, nuclear radiation-hardening and biological properties of the coating materials. Examples of other coating materials include carnauba wax, ethyl cellulose, ethylene maleic anhydride copolymer, methyl vinyl ether, octadecyl vinyl ether, phenoxy resin, poly 2-ethylhexyl methacrylate, poly (caprolactone), poly (caprolactone) triol, poly-1-butadiene, poly-n-butyl acrylate, poly-p-vinyl phenol, polybutadiene oxide, polybutadiene hydroxy terminated, polybutadiene-methylacrylated, polycutadiene acrylonitrile, polydecyl acetate, polyethyl acrylate, polyethylene, polyethylene glycol methyl ether, polyhexyl methacrylate, poly 1 butene, polymethacrylate, polystyrene, polyvinyl butyryl, polyvinyl carbazone, polyvinyl chloride, polyvinyl isobutyl ether, polyvinyl methyl ether, polyvinyl stearate, and vinyl alcohol/vinyl/actate copolymer.

In most cases, oligonucleotides such as DNA have to be attached onto SERS active substrates which can have as its support a glass microscope slide, a surface of a fiberoptic probe biosensor, a fiberoptic probe biosensor array, a waveguide or waveguide microsensor arrays. Since most of SERS coatings are based on silver or gold, the binding of oligonucleotides on the metal surface can be based on thiol chemistry or other standard chemical binding methods. The thiols are known to strongly chemisorb to silver and gold surfaces to form monolayers that possess supramolecular properties, as found in G. Whitesides and P. Laibnis, *Langmuir*, 6, 87–95, 1990, incorporated herein by reference.

If the overcoat is silica, the gene probe is bound to the silica coating. The silica surface is derivatized with silane by incubation in a 2% 3-aminopropyl triethoxysilane (APTS) for 24 hr. at room temperature, washed in acetone and dried in vacuum. The silanyl groups are activated by incubation in 1% glutaraldehyde in water for one hour at room temperature. Excess glutaraldehyde is removed by washing in water and rinsing with phosphate buffered saline (PBS). Oligonucleotide probe molecules containing amino linkers are attached to the silica surface by incubating for 24 hr at 4° C. with a probe solution (e.g., concentration 10 mg/ml). Unbound probe is washed away with PBS. A. Pal et al, *Analytical Chemistry*, 67, 3154, 1995, is incorporated herein by reference.

The oligonucleotide strand of the SER gene probe is complementary to a target oligonucleotide strand when the SER gene probe is immobilized on the SERS active substrate. The SERS label is unique for a particular target oligonucleotide of a particular sequence that is characteristic of a particular bacteria or virus. So, if there are more than one SER gene probe utilized to assay for more than one particular oligonucleotide sequence characteristic of a particular bacteria or virus, then each SER gene probe that is unique for a particular target oligonucleotide strand will have a different, separate unique SERS label. Target oligonucleotide strands in a multiple assay having the same sequence are designated for the same SERS label.

FIG. 1 is a schematic diagram of a SERS gene probe detection system 1. The system comprises an energy source 5, a bandpass filter 10, a mirror 15, a SERS active substrate 20, the SERS active substrate 20 having SER gene probes 25, a collection of optics 30, a Raman holographic filter 35, optical fiber 40, coupling optics 45, a detector 50 being a signal analyzer and a data processor 55. The bandpass filter 10 and the mirror 15 provide a means for transmitting optical energy from the energy source 5 to the SERS active substrate 20 to generate a Raman optical signal from the SER gene probe 25 being labeled with a SERS label. The collection of optics 30, the Raman holographic filter 35, the optical fiber 40 and the coupling optics 45 provide a means for collecting the Raman optical signal and transmitting the signal for detection by a signal analyzer 50. The signal analyzer 50 and the data processor 55 provide an analyzing means for detecting and identifying hybridized target oligonucleotide strands.

Instrumentation for the experimental was as follows. Raman measurements were conducted with a SPEX Model 1403 double-grating spectrometer (SPEX Inc.) equipped with a thermoelectrically cooled gallium arsenide photomultiplier tube (RCA, Model C31034), operated in the single-photoncounting mode. Data storage and processing were handled using a personal computer (PC) with SPEX Datamate software. The monochromator bandpass was 2 cm$^{-1}$. Laser excitation was the 620 nm line extracted from the emission band of a rhodamine 6G loaded dye laser (Coherent, CR-599-21) pumped by an argon ion laser (Coherent, Innova-70). Tuning of a birefringent filter plus the use of a bandpass filter permitted a narrow excitation bandpass centered at 620 nm. Laser power was 25 mW for all measurements. A right-angle geometry of the laser excitation source and the scattered radiation was employed. SERS measurements were performed using two experimental systems. The SPEX-based system was used to generate the basic SERS spectra. An ICCD-based system was used to generate spectra in hybridized experiments. In this system, the 632.8-nm line from a helium-neon laser was used with an excitation power of approximately 5 mW. A bandpass filter was used to spectrally isolate the 632.8-nm line before focusing onto the sample. Scattered radiation was collected with a two-lens system which efficiently coupled the collected radiation to a 600 μm diameter silica fiber (NA-0.26, General Fiber Optics). Signal collection was performed at 180° with respect to the incident laser beam. A Raman holographic filter was used to reject the Rayleigh scattered radiation prior to entering the collection fiber. The collection fiber was finally coupled to a spectrograph (ISA, HR-320) which was equipped with a red-enhanced intensified charge-coupled device (RE-ICCD) detection system (Princeton Instruments, RE-ICCD-576S). ICCD control and data processing was enabled by a Princeton Instruments ST-130 control unit and CSMA software installed on a PC. Fluorescence measurements were performed with the Perkin-Elmer fluorimeter (Model LS-50).

The agglomerate-free alumina (0.1 μm nominal particle diameter) used to prepare the SERS substrates was provided by Baikowski Int. Corp. The alumina was suspended in distilled Milli-Q Plus water by sonication.

The highest grade of reagents available were used. All solutions were prepared with distilled, deionized Milli-Q Plus water. All nucleic acid solutions were sterilized by autoclaving or by filtration through a 0.22-μm filter. Exposure of labeled DNA to light was minimized by using opaque siliconized glassware, aluminum foil covering, or reduced room-lighting conditions.

Figure 2:
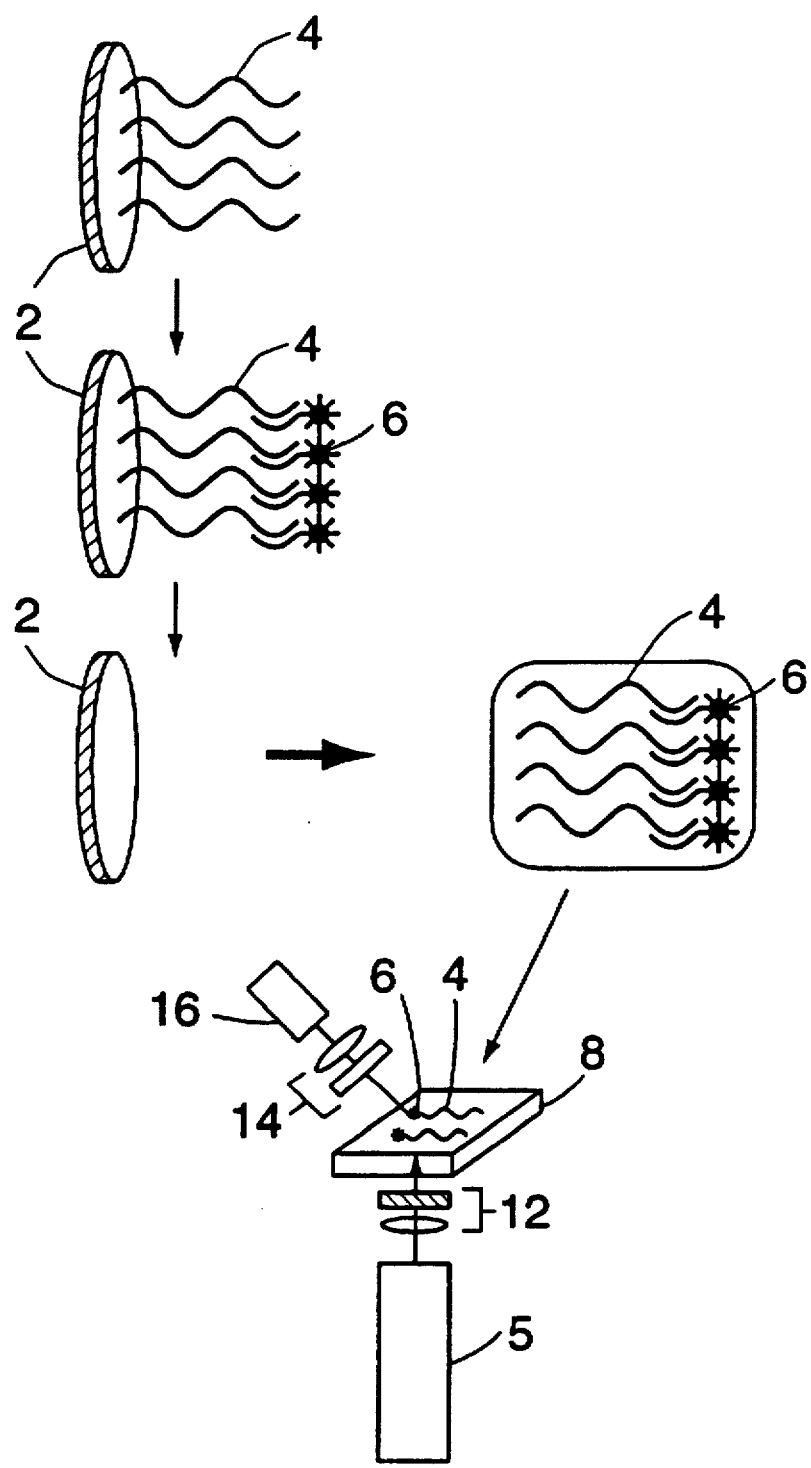
FIG. 2 shows a diagram of the method of using a SER Gene Probe for hybridization and detection with the SER Gene Probe attached to the nucleotide strands to be identified.

The following Example 1 describes the method depicted by FIG. 2.

EXAMPLE 1

SERS active substrates were prepared in the following manner. A rectangular glass strip (2.5 cm×1.25 cm; 1 mm thick) was cut from a microscope slide that served as the support base. The glass strip was then cleaned with nitric acid, distilled water, and ethnology and dried using a stream of dried air. Alumina microparticles were used to form a microstructured surface. Three drops of a 5% aqueous suspension of alumina (type 0.1 CR) were delivered and evenly spread on the glass strip. The glass strip was then placed on a conventional spinning device to uniformly spread the alumina on the surface of the glass. The glass strip was spun at 2000 rpm. Then, a 100-nm layer of silver was thermally evaporated onto the alumina-coated glass strip in a vacuum evaporator at a pressure of $2 \times 10^6$ torr to form the metal layer with a deposition rate of 2 nm/s.

Preparation of the Nitrocellulose Blot

Oligonucleotides for binding to nitrocellulose were prepared from homopolymers of adenosine or thymidine. Samples were heated for 10 minutes at 100° C., rapidly chilled on ice and diluted to 50% with 1M NaOH. Alkaline-treated DNA was then incubated for 30 minutes at room temperature before neutralization with the following solution: 0.5-M Tris, 1M NaCl, 0.3M sodium citrate, 1M HCl.

Samples were then immediately chilled on crushed ice. A nitrocellulose filter (Sigma) was cut into 3 mm×3 mm squares and turned onto virgin parafilm. DNA (25 μL) was loaded onto the nitrocellulose in 5 μL aliquots, added sequentially to the same spot, leaving sufficient time to absorb the material between additions. The amount of DNA affixed to the membrane was 2.5 μg. Filters were air dried for 2 h and then washed with 50 mL of SSC-20X solution (175.3 g of NaCl, 88.2 g of Na citrate in 1 L H$_2$O; pH 7.0). After washing the DNA loaded nitrocellulose, the filters were redried and baked for 2 h at 75°–85° C. in a vacuum oven. FIG. 2 shows the nitrocellulose filter 2 with immobilized DNA 4 adsorbed thereon.

Synthesis of SER Gene Probes

Various DNA probes having different SERS labels were prepared. Solutions of cresyl fast violet (Fluka), erythrosin, and aminoacridine (Sigma) were prepared at 0.15–0.25M concentration. Labeled oligonucleotides were synthesized as 5' phosphoramidates using a modification of the procedure described by Chu et al *Nucleic Acids Res.*, 1983, 11, 6513, incorporated herein as a reference. Briefly, solutions of deoxyribonucleotide oligomers (either 9 or 18 residues in length; (Sigma) were converted to 5'-phosphor-oimidazolide intermediates with 0.2M imidazole and 0.5M 1-ethyl-3-dimethylamino)propyl carbodiimide by incubation at 50° C. for 3 h. The 5'-phosphorimidazolides were then reacted with equal volumes of the SERS active labels (e.g., cresyl fast violet dye) for 18 h at 50° C. Unreacted label was removed from the reaction mixture by gel mixture by gel filtration on Biospin 6 columns (Bio-Rad). The resultant labeled oligonucleotide samples 6 were concentrated by lyophilization.

Hybridization Procedures

Nitrocellulose filters 2 containing the DNA to be hybridized 4 were placed in siliconized 1.5 mL microfuge tubes. Distilled water was added to the tube and was boiled in a water bath. The water was then removed by gentle aspiration. Negative controls consisted of labeled DNA that was not complimentary to the immobilized DNA.

The filters 2 were incubated overnight at 40° C. in hybridization solutions containing 2 ng/mL of the labeled probe 6. DNA which did not hybridize was removed by washing three times with SSPE-20X solution (174 g of NaCl, 27.6 g of NaH$_2$PO$_4$ in 1 L of H$_2$O; pH 7.4) containing 0.1% SDS at room temperature.

Material which hybridized 4,6 to the nitrocellulose 2 was recovered as follows. Filters were washed twice with 1 mL of SSC solution (0.1 N NaOH) for 30 minutes at room temperature and three times with 1 mL of SSC, followed by vortexing. The wash buffer was aspirated, neutralized, pooled, and lyophilized before SERS analysis. The reconstitution volume was 30 μL, and only 1 μL 4,6 was spotted onto the SERS substrate 8.

Referring to FIG. 2, an energy source 5 generates the exciting optical energy and the exciting optical energy is transmitted by a transmitting means 12 to the hybridized oligonucleotide material 4,6 on the SERS active substrate 8. A Raman optical signal is generated and is collected and transmitted by means 14 to a signal analyzer 16 for detection. The means for transmitting exciting optical energy includes filters and mirrors as well as optical fibers. The means for collecting and transmitting the optical signal from the SERS active substrate include a collection of optics such as lenses, mirrors and/or filters as well as optical fibers.

The method of FIG. 2 can also utilize microparticulates as the sampling medium, wherein the oligonucleotide strands of known sequence are immobilized onto the microparticulates. These microparticulates comprise microspheres, magnetic particles, magnetic particles coated with polymer or other microstructures. Then, instead of recovering the hybridized oligonucleotide material from the sample medium and transferring a small amount to a SERS active substrate, the amount transferred would include the microparticulates with the hybridized material still attached. The need to recover the hybridized oligonucleotide material from the sample medium is eliminated. When magnetic particles are used means for attracting the magnetic particulates can be used for the transfer process.

Figure 3A:
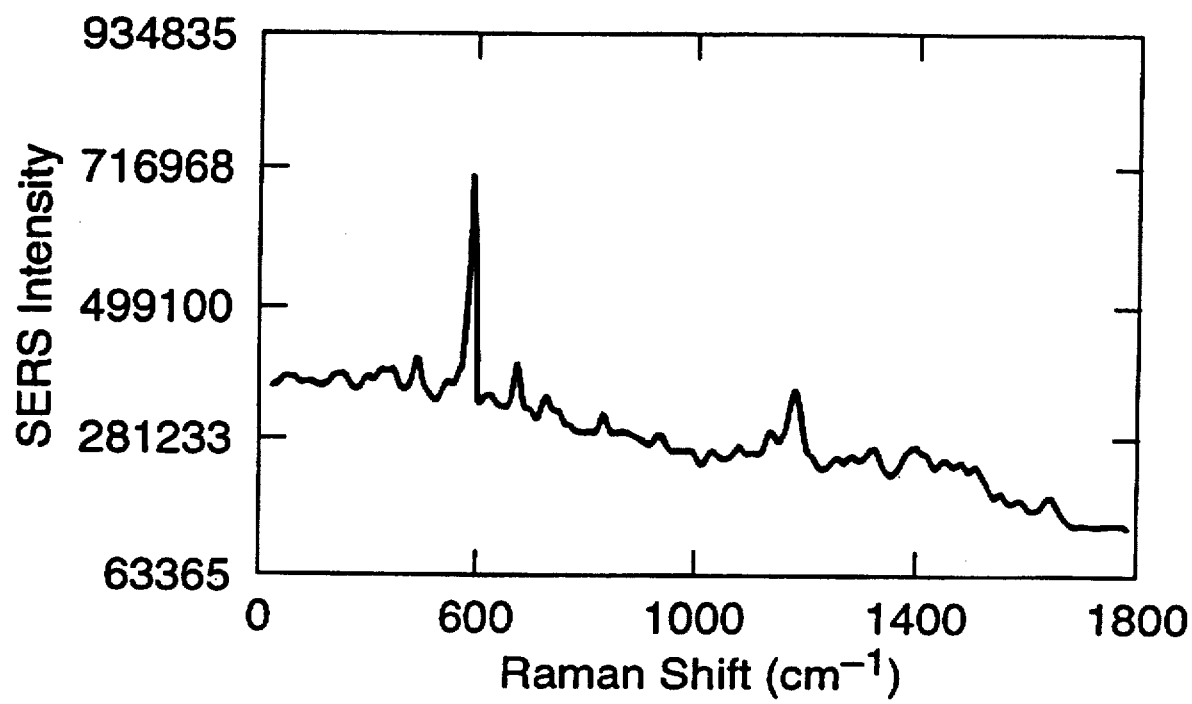
FIG. 3a is a SERS Spectrum of only cresyl fast violet label.

FIG. 3a shows a SERS spectrum of a dye, cresyl fast violet (CFV), that was used in Example 1 for DNA labeling. The measurement was performed using a silver-coated alumina substrate. The laser wavelength was 620 nm, and the excitation power only 25 mW. The SERS spectrum of cresyl violet exhibits a series of narrow lines with the strongest at 590 $cm^1$. This intense and sharp line can be attributed to the benzene ring deformation mode. Another less intense but sharp line at 1195 $cm^1$ could be related to benzene ring breathing vibrations. Another group of small peaks between 1000 and 1400 $cm^1$ could be associated with aromatic ring substitution-sensitive modes. Finally several peaks, which could correspond to benzene stretch vibrations, occur between 1500 and 1650 $cm^1$.

Figure 3B:
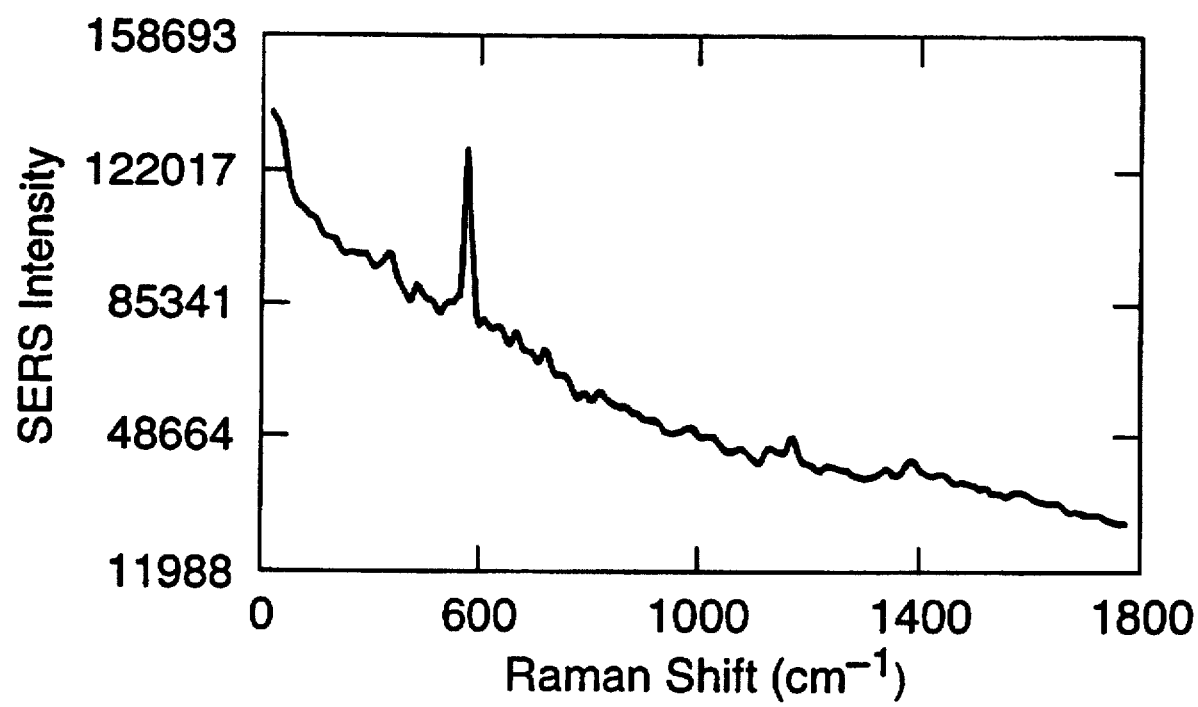
FIG. 3b is a SERS Spectrum of cresyl fast violet label attached to 18 deoxyribonucleotide oligomers, $p(dT)_{18}$.

Cresyl fast violet, which was used as the model DNA label in Example 1, was covalently attached to a nucleic acid fragment consisting of 18 deoxyribonucleotide oligomers of thymine, $p(dT)_{18}$. The SERS spectrum of this labeled DNA fragment is shown in FIG. 3b. The SERS-active substrate used for this figure is identical to that used to obtain the SERS spectrum of the CFV label alone in FIG. 3a. FIG. 3b demonstrates that it is possible to detect the spectral characteristic features of the CFV label even when it is bound to a large $p(dT)_{18}$ oligonucleotide gragment. Comparison of FIG. 3a and 3b indicates that the presence of the oligonucleotides induces a decrease in the SERS intensity of the CFV label, but the features of the label are still visible. Although there is an increase of the background emission when the CFV label is attached to the DNA fragment, the sharp peak associated with the label at 585 $cm^1$ remains the most prominent SERS line of the labeled DNA fragment. A slight shift of this band is observed between the labeled dye (585 $cm^1$, FIG. 3b) and the dye alone (590 $cm^1$, FIG. 3a). Careful inspection of FIG. 3b indicates that several other small peaks in the label oligonucleotide system (445, 490, 675, 725, 1140, 1180 $cm^1$, FIG. 3b) are similar to those detected in the label (450, 490, 675, 730, 1145, 1195 $cm^1$, FIG. 3a).

Different SERS labels can be used for different target oligonucleotide strands of different sequences and different bacterial and viral types. SERS labels that can be used include cresyl fast violet, cresyl blue violet, erythrosin, as well as aminoacridine. Other labels that exhibit a characteristic Raman or SERS emission can also be used, as long as the label doesn't interfere with hybridization. The chemical structure or substituent to be used as a SERS label is not present in the original native DNA. Some chemical structures that can be used as a SERS label and are inert to hybridization include cyanide (CN), thiol group (SH), chlorine (Cl), bromine (Br) and phosphorus (P). The SERS label can be attached at the end of the oligonucleotide strand or it can be disposed with the oligonucleotide strand. More than one SERS label can be used on a given oligonucleotide strand. Another embodiment is one in which two oligonucleotide strands are used for the SER gene probe and the SERS label is disposed intercalated between the two strands. This particular embodiment provides the label to be held in place by the two strands. There is no attachment of the label on the oligonucleotide strands. More than one SERS label may be used for this embodiment as well.

To demonstrate the applicability of the SERS method in DNA gene probe technology, a series of hybridization and SERS detection experiments were performed. Hybridization, which involves the joining of a strand of nucleic acid with its corresponding mirror image, is a powerful technique to identify DNA sequences of interest. FIG. 2 shows a schematic diagram of the hybridization and SERS detection of the probes. FIG. 4 shows the results obtained with the different samples investigated. In these experiments, DNA fragments to be hybridized were employed, viz., $p(dA)_{18}$ oligonucleotides which are complementary to the SERS labeled $p(dT)_{18}$ probes discussed previously. The SERS labeled probes that hybridized to the DNA oligomers attached on nitrocellulose were recovered by washing the nitrocellulose and spotted on a SERS active substrate (silver-coated alumina) for analysis. Negative controls, which consisted of labeled DNA that was not complementary to $poly(dT)_{18}$ fragments, for example, CFV-labeled $p(dC)_9$ oligonucleotides, were also analyzed. FIG. 4a shows clearly the SERS peak of the labeled $p(dT)_{18}$ probes that have hybridized to $p(dA)_{18}$. On the other hand, negative controls exhibit no SERS signals since the SER gene probes do not hybridize to the $p(dC)_9$ oligonucleotides (FIG. 4b).

Because SER gene probes rely on chemical identification, rather than emission of radioactivity, they have a significant advantage over radioactive probes. SER gene probes are formed with stable chemicals which do not emit potentially dangerous ionizing radiation. Furthermore, the probes offer the excellent specificity inherent to Raman spectroscopy. While isotope labels are few, many chemicals can be used to label DNA for SERS detection. Potentially up to hundreds of different SER gene probes can be constructed. A large number of probes with different labels could be used to simultaneously probe one immobilized DNA, PNA or RNA of interest.

Recently, luminescence labels (e.g., fluorescent or chemiluminescent labels) have been developed for gene detection. Although sensitivities achieved by luminescence techniques are adequate, alternative techniques with improved spectral selectivities must be developed to overcome the need for radioactive labels and the poor spectral specificity of luminescent labels.

Figure 5A:
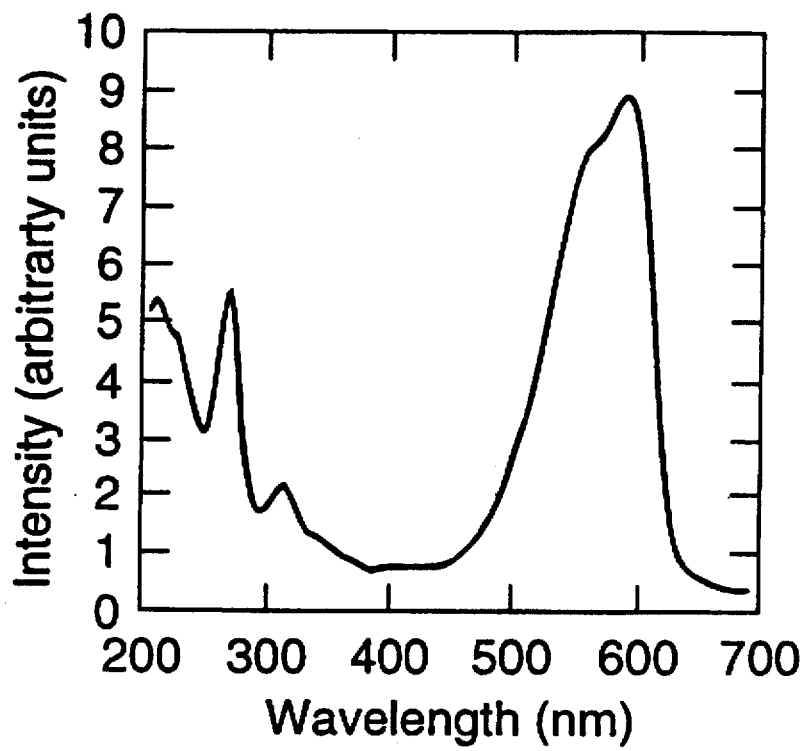
FIG. 5a shows the absorption spectrum of cresyl fast violet.
Figure 5B:
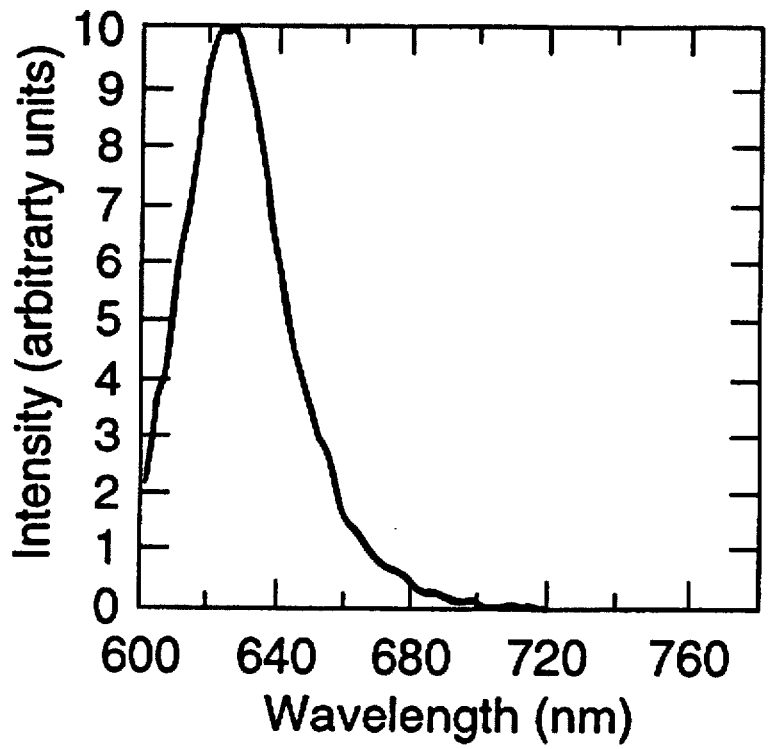
FIG. 5b shows the fluorescence spectrum of cresyl fast violet.

The spectral specificity of the SER gene probe is excellent in comparison to the other spectroscopic alternatives. For comparison purposes, the detection of the dye cresyl violet in UV absorption, fluorescence and SERS is compared. As shown in FIG. 5, the spectral bandwidth of cresyl fast-violet in UV absorption and fluorescence are broad (typically 50–100 nm half-widths), whereas the bandwidth of the SERS spectrum of the same CFV dye is much narrower (<1 nm half-width, limited here by Raman spectrometer resolution; see FIG. 3). For this reason, the Raman approach has a major advantage over the absorption or luminescence techniques. In a typical Raman spectrum, a spectral interval of at least 2000 cm$^1$ can provide 2000/2 or 10 available individual spectral "intervals" at any given time. Even allowing a factor of 10 due to possible spectral overlap, it should be possible to find 10 labels that can be used for simultaneous detection of different gene biotargets.

The method of FIG. 2 can incorporate a blotting procedure such as the Southern blotting technique, the Western blotting technique or the Northern blotting technique. A blotting technique provides an alternate method of recovering the hybridized oligonucleotide material from the nitrocellulose filter and transferring combined into one step, by simply blotting the hybridized oligonucleotide material directly onto the SERS active substrate. The small amount needed to be transferred onto the substrate is an amount sufficient enough as to provide a detectable quantity of hybridized oligonucleotide material to the SERS active substrate.

Figure 6A:
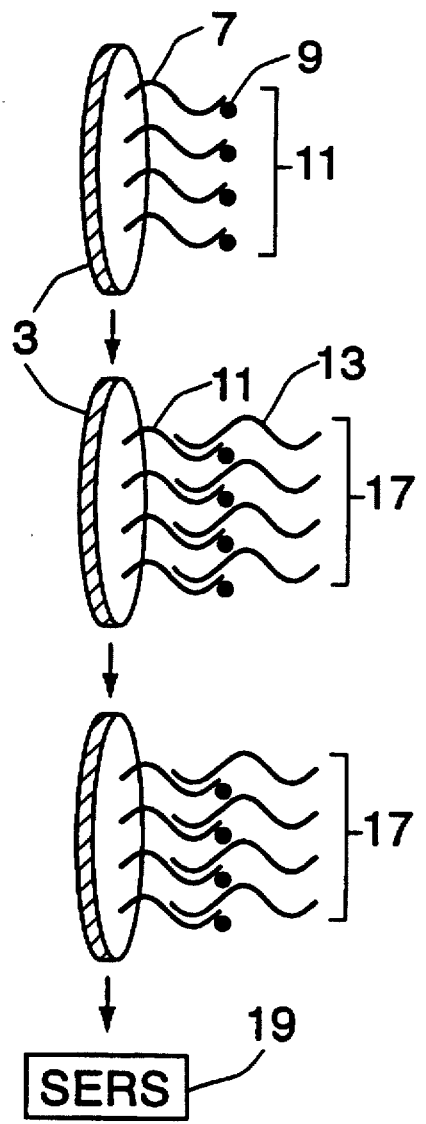
FIG. 6a is a diagram illustrating the method of direct detection with the SER Gene Probe being attached to the SERS Active Substrate.
Figure 6B:
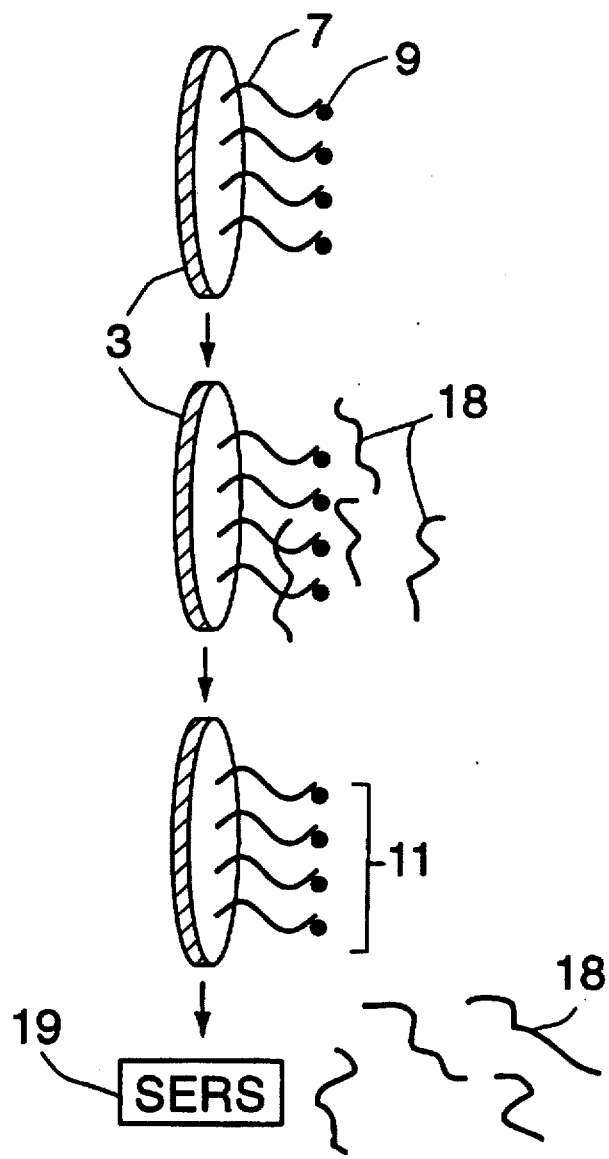
FIG. 6b illustrates the same direct detection method as FIG. 6a, except no hybridization occurs due to absence of target oligonucleotides.

FIG. 6 illustrates a method for using SER gene probes as biosensors for hybridization and direct detection of the SERS label to identify the target oligonucleotide strands which are hybridized to the SER gene probes. Referring to FIG. 6, a SERS active substrate 3 is prepared as previously described with the SER gene probe attached to the substrate. The SER gene probe 11 comprises at least one oligonucleotide strand 7 of known sequence labeled with a SERS label 9 which is unique for a target oligonucleotide strand of a particular sequence. The oligonucleotide strand of the SER gene probe is complementary to the target oligonucleotide strand of which the SERS label is designated for. Following the hybridization step as previously described, the SER gene probe 11 is hybridized with the target oligonucleotide 13 of which it is unique. FIG. 6a demonstrates hybridization 17 when target oligonucleotides 13 are present in a sample. FIG. 6b demonstrates non-hybridization due to the absence of target oligonucleotides. FIG. 6b shows that upon washing the oligonucleotides that are not complementary to the SER gene probes 18 away, the SER gene probes 11 are left unhybridized. Once hybridization has taken place and the substrates washed to rid the unhybridized oligonucleotides 18, the SERS active substrate is analyzed 19. Due to the different hybridization state, the SERS gene probe in FIG. 6a (positive hybridization) and in FIG. 6b (non-hybridization), will exhibit different SERS signals.

Figure 7:
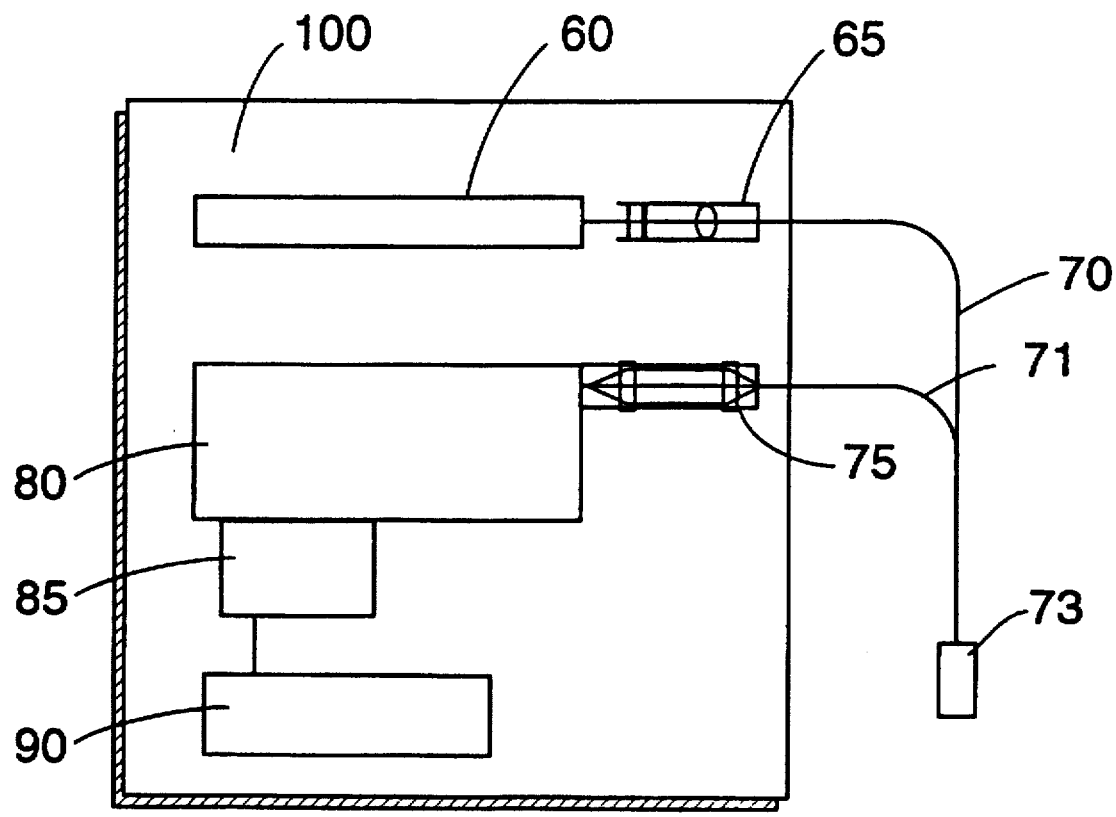
FIG. 7 is a schematic diagram of a SER Gene Probe Fiberoptic Biosensor.

FIG. 7 is a schematic diagram of a SER gene probe fiberoptic biosensor. Here, the SERS active substrate is disposed on the biosensor tip by bonding means such as adhesive or a SERS active substrate has been formed on the biosensor tip making the tip the SERS active substrate. The formation of a SERS active substrate has been previously described. The SER gene probe fiberoptic biosensor 73 is introduced into a sample to be analyzed. Exciting optical energy from energy source 60 is transmitted by an optical fiber 70 through a bandpass filter 65 to the SER gene probe on the fiberoptic probe tip 73 generating a Raman optical signal from the SERS label. The optical signal is collected and transmitted through the optical fiber 71 and coupling optics 75 to the spectrograph 80 to the detector 85 and to the controller 90. The energy source, bandpass filter, coupling optics, spectrograph, detector and the controller are a portable SERS monitor 100. FIG. 8 is a close-up view of 73 in FIG. 7. FIG. 8a shows how exciting optical energy 63 enters the optical fiber and is transmitted to the SER gene probe 11 on the SERS active substrate 3, then how the optical signal 83 is collected and is transmitted back through the optical fiber and to a signal analyzer. FIG. 8b shows an alternate embodiment of FIG. 8a wherein the optical fiber is tapered. FIG. 9 shows another embodiment of FIG. 8 where more than one optical fiber is used, one for the excitation fiber and the other for the collection fiber to collect and transmit the signal to the signal analyzer. Here, a mirror 95 is used to further direct the optical energy onto the SERS substrate 3 and onto the SER gene probe 11.

Figure 10:
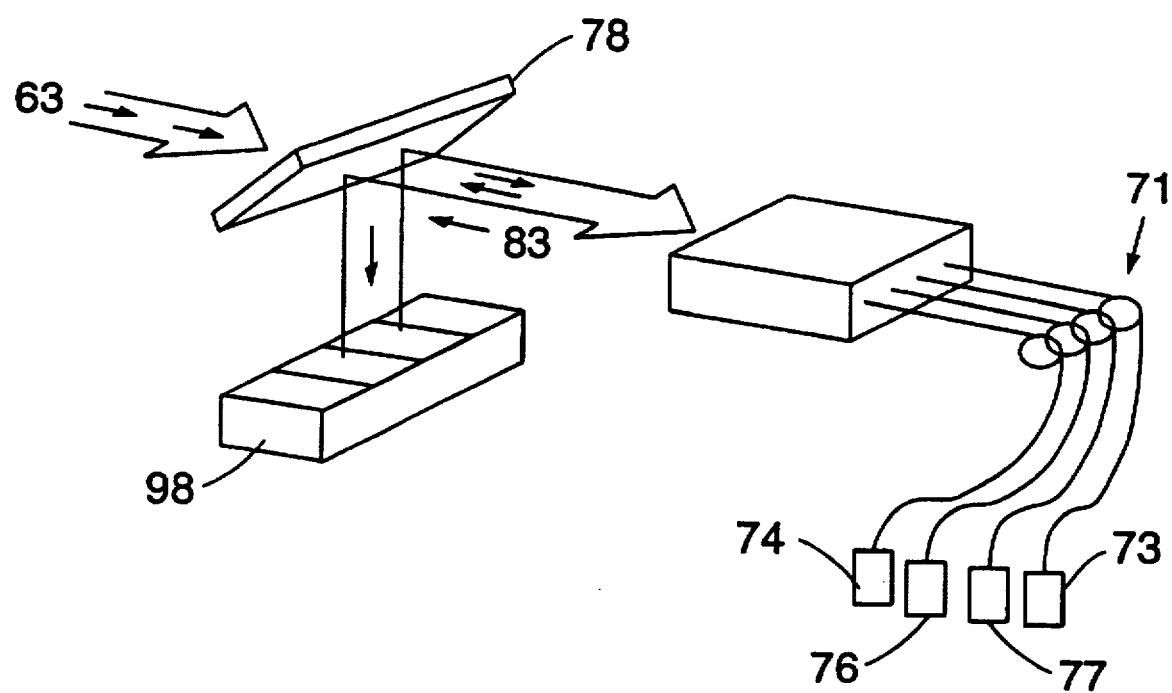
FIG. 10 is a schematic diagram of an array of SER Gene Probe Fiberoptic Biosensors each having a SERS active substrate with immobilized SER Gene Probes used for conducting simultaneous multiple assays.

FIG. 10 shows an array of SER gene probe fiberoptic biosensors 73, 74, 76, 77 each having a SERS active substrate with immobilized SER gene probes attached to the biosensor tip. The device of FIG. 10 is capable of simultaneously performing multiple assays. Optical energy 63 from an optical energy source is directed through a beam splitter 78 and onto a fiberoptic array of multiple optical fibers 71 leading to separate fiberoptic biosensors 73, 74, 76, 77 having different SER gene probes unique for their different and separate complementary target oligonucleotides. The optical signals generated from the SERS labels are collected and transmitted by the array of optical fibers 71 to a detection array 98 where the signals are analyzed.

Figure 11:
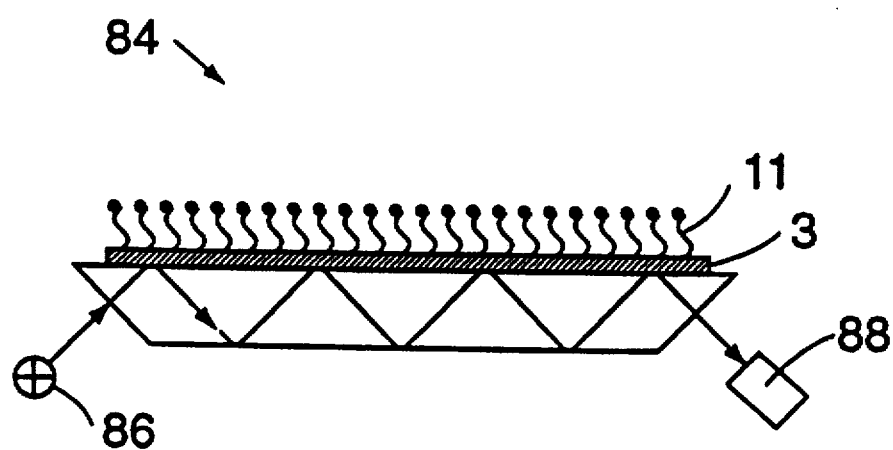
FIG. 11 illustrates SER Gene Probes attached to a SERS active substrate on the surface of a Waveguide Biosensor.

FIG. 11 shows a waveguide biosensor 84 that has a SERS active substrate 3 on its surface. The SERS active substrate 3 has several SER gene probes 11 attached thereto. Once again, the exciting optical energy from an energy source 86 is transmitted through the waveguide using appropriate optics and filters to the surface of the waveguide to the SERS active substrate 3 and to the SER gene probes 11 to generate an optical signal. The optical signal is transmitted using appropriate optics and filters to the signal analyzer 88.

Since the SERS peaks are narrow, it is possible to detect several SERS labels by spectral discriminating. Therefore, it is possible to attach several types of probes (probes for different SERS labels) on a single waveguide or a single optical fiber and detect several oligonucleotide strands simultaneously.

Figure 12:
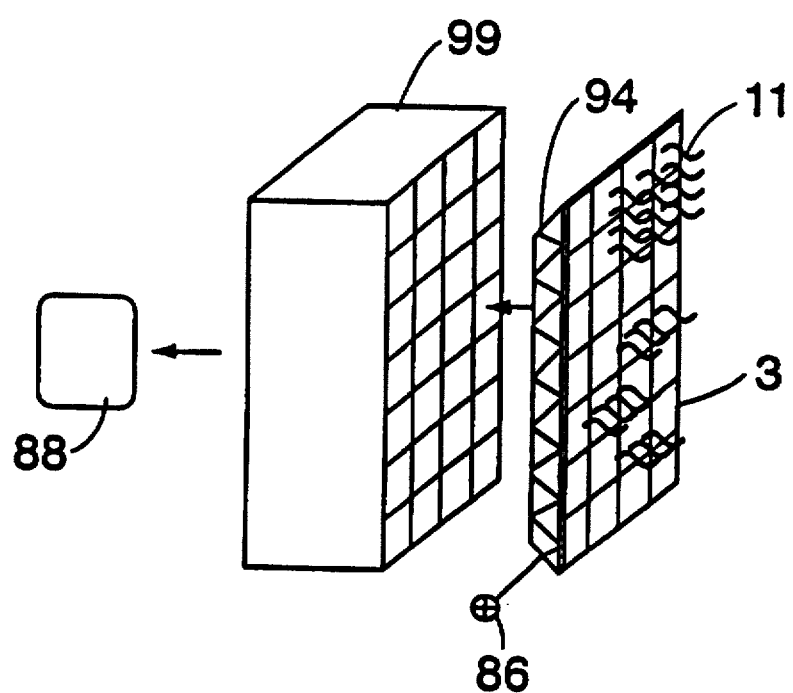
FIG. 12 is a diagram of SER Gene Probes attached on a SERS active substrate on the surface of waveguide microsensor arrays with charge-coupled devices or photodiode arrays.

FIG. 12 is a diagram of SER gene probes 11 attached on a SERS active substrate 3 on the surface of waveguide microsensor arrays 94 with charge-coupled devices 99 or photodiode arrays. According to FIG. 12, optical energy from an energy source 86 is transmitted through the waveguide 94 to the surface of the waveguide arrays and to the SERS active substrates 3, to the SER gene probes 11 to generate an optical signal. The optical signal is transmitted to the two dimensional chargecoupled device detector (CCD) 99 and the data is sent for SERS recording and processing 88. A CCD system is described by Yung-Fong Cheng et al, *Appl. Spect.*, 44, 755–765, (1990), incorporated herein as a reference. The system in the described in the reference, however, unites CCD with capillary-zone electrophoresis rather than with a SERS biosensor.

Figure 13:
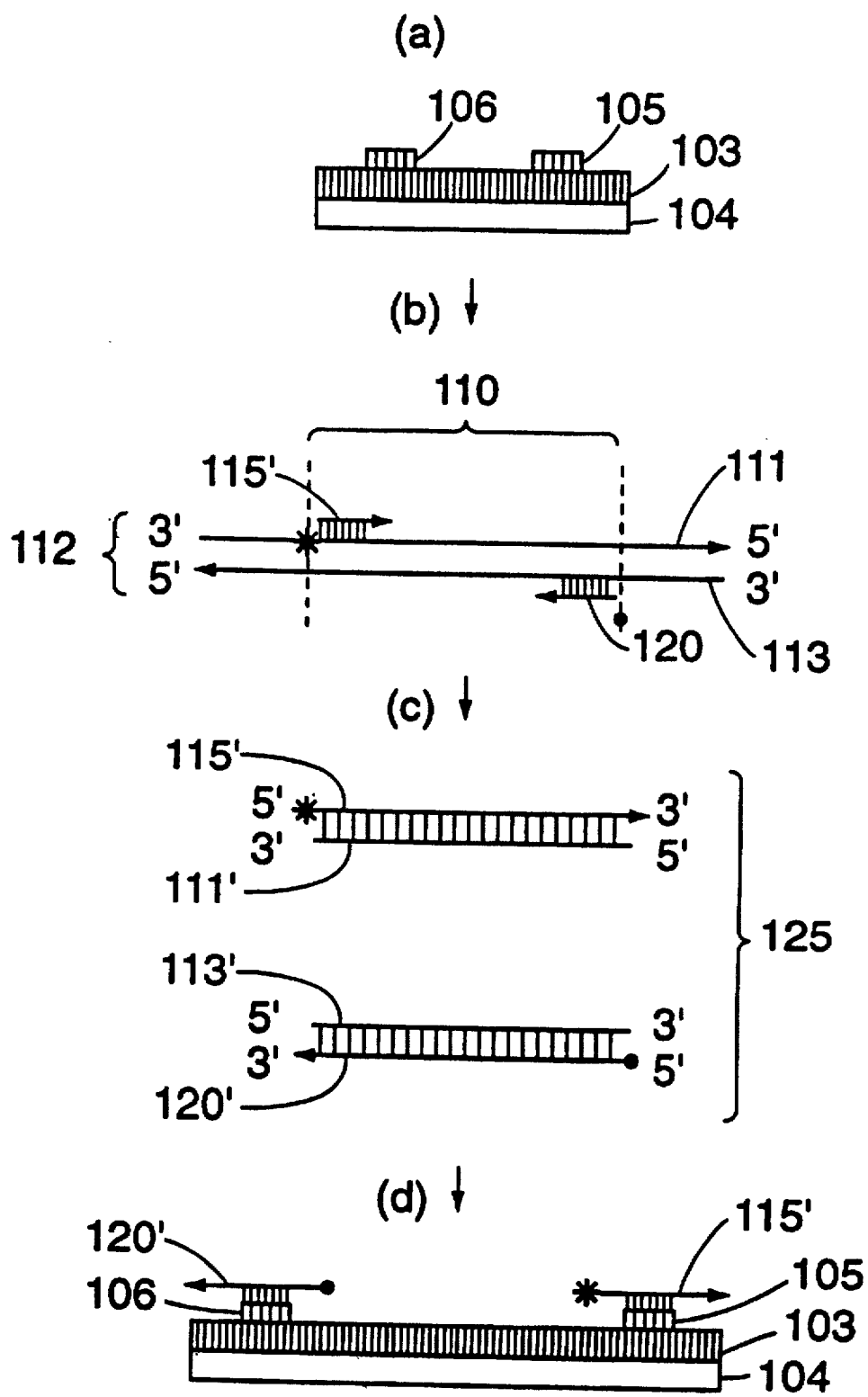
FIG. 13 illustrates a method for using the SER gene probe in conjunction with Polymerase Chain Reaction to detect target oligonucleotide strands.

FIG. 13 illustrates a method for using the SER gene probe in conjunction with polymerase chain reaction PCR) to detect target DNA strands. In this method, unlabeled DNA strands of known sequences 105 and 106, complementary to the double-stranded target DNA 112, respectively, are adsorbed onto a SERS active substrate 103 (step a, FIG. 13). The SERS active substrate 103 is shown on the surface of support base 104. The SER gene probes 115 and 120 are synthesized and used as SERS labeled primers. One or two labeled primers can be used. In FIG. 13, these primers 115 and 120, of approximately 20 bases, are complementary to sites on the opposite DNA strands on either side of the double-stranded target DNA 111 and 113. Note that each primer hybridizes to the opposite strand. Then, PCR is performed in the following nanmer: (step b) the DNA strands are isolated and denatured to form single-stranded templates by heating to 90°–95° C. for approximately 1 minute. The two primers 115 and 120 are annealed to the isolated single stranded DNA templates at 40°–60° C. and then cooled for about 2 minutes and (step c) DNA polymerase (purified from the thermophilic bacterium *Thennus aquaticus*, Taq DNA polymerase) is added at about 72° C. for about 2 minutes, resulting in extension of the DNA molecule (amplification) through the target region 110 of the DNA strand 112. (Step d) Following amplification by PCR, the SERS active substrate 103 on a support base 104 is immersed and incubated in the sample containing the amplified products 125, which are the SERS labeled amplified DNA segments, for a sufficient time as for hybridization between the SERS labeled amplified DNA segments and the unlabeled DNA strands 105, 106 on the substrate 103 to occur to completion and a SERS signal can be detected. The SERS active substrate having the unlabeled DNA strands complementary to the target DNA strand will detect the labeled amplified products. Following multiple cycles, there has been exponential amplification of the target region 110 containing SERS labeled primers 115 and 120. Therefore, the SERS labeled primers 115 and 120 have been amplified as well. This process can be repeated through any number of cycles to yield many copies of the target sequence. While there has been shown and described what are at present considered the preferred embodiments of the invention, it will be obvious to those skilled in the art that various changes and modifications can be made therein, without departing from the scope of the invention defined by the appended claims.

what is claimed is:

1. A method for using a SER gene probe for detection and identification of target DNA strands that have been amplified through Polymerase Chain Reaction comprising the steps of:

a) preparing a SERS active substrate having adsorbed thereon at least one unlabeled DNA strands of known sequence, being complementary to a target region of a target DNA strand, said target DNA strand comprising double strands of DNA complementary to one another, and said SERS active substrate being disposed on a support means;

b) synthesizing at least one SER gene probe as a primer wherein said SER gene probes comprises an oligonucleotide strand complementary to sites on the opposite DNA strands of said target DNA strand wherein said primer has a sequence which is identical to the 5' end of one DNA strand of said target DNA strand, said SER gene probe further comprises a SERS label attached to said oligonucleotide strand;

c) heating said target DNA strand to a temperature sufficient for denaturization of said double strands of said target DNA to occur to form single-stranded DNA templates;

d) annealing said primer to said DNA template at a temperature sufficient for said primer to bind to said complementary sequence at the 3' end of said opposite DNA strand of said target DNA strand;

e) adding DNA polymerase to extend the DNA molecule through said target region of said target DNA strand yielding amplified products, said amplified products being SERS labeled amplified DNA segments;

f) immersing said SERS active substrate in a sample containing said amplified products;

g) incubating said SERS active substrate in said sample for a time sufficient enough as for hybridization between said SERS labeled amplified DNA segments and said unlabeled DNA strands on said substrate to occur to completion and a SERS signal is detected; and h) analyzing said SERS signal.

2. The method of claim 1, wherein said support means is a fiberoptic probe having a probe tip which supports said SERS active substrate, said fiberoptic probe further having at least one optical fiber for transmitting exciting optical energy from an energy source to said SER gene probe on said SERS active substrate on said fiberoptic probe tip to generate a Raman optical signal and for collecting and transmitting said Raman optical signal to a signal analyzer.

3. The method of claim 1, wherein said support means is a waveguide having a surface which supports said SERS active substrate, said waveguide further having means for transmitting exciting optical energy from an energy source to said surface and to said SER gene probe to generate a Raman optical signal and means for collecting and transmitting said Raman optical signal to a signal analyzer.

* * * * *